US00PP15507P2

(12) United States Plant Patent
Olesen et al.

(10) Patent No.: US PP15,507 P2
(45) Date of Patent: Feb. 1, 2005

(54) **COMPACT *FLORIBUNDA* ROSE PLANT 'POULAC004'**

(50) Latin Name: *Rosa hybrida*
Varietal Denomination: POULac004

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 99 days.

(21) Appl. No.: 10/345,421

(22) Filed: Jan. 14, 2003

(51) Int. Cl.[7] ..... A01H 5/00
(52) U.S. Cl. ..... Plt./150
(58) Field of Search ..... Plt./150

(56) References Cited

U.S. PATENT DOCUMENTS

PP11,598 P * 10/2000 Olesen et al. ..... Plt./143

OTHER PUBLICATIONS

UPOV ROM GTITM Computer Database, GTI JOUVE Retrieval Software 2003/01 citation(s) for 'POULAC004'.*

* cited by examiner

*Primary Examiner*—Bruce R. Campell
*Assistant Examiner*—W C Haas

(57) ABSTRACT

A new Compact *Floribunda* rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification: Botanical: *Rosa hybrida* 'POULac004'. Commercial: Compact *Floribunda*.

SUMMARY OF THE INVENTION

The present invention constitutes a new and distinct variety of compact *floribunda* rose plant which originated from a controlled crossing between an unnamed seedling, non-patented, and an unnamed seedling, non-patented. The two parents were crossed and the resulting seeds were planted in a controlled environment. The new variety is named 'POULac004'.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULac004' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULac004' was selected by the inventors as a single plant from the progeny of the hybridization in April 2000.

Asexual reproduction of 'POULac004' by cuttings and traditional budding was first done by L. Pernille and Mogens N. Olesen in their nursery in Fredensborg, Denmark in June, 2000. This initial and other subsequent propagations conducted in controlled environments have demonstrated that the characteristics of 'POULac004' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac004'. Specifically illustrated in the drawing:

1. Stem showing branching and the attachment of leaves, buds, and peduncles;

2. Flower bud, partially opened bud, and open bloom;

3. Flower petals, detached;

4. Sepals, receptacle, and pedicel;

5. Stem as well as a bare stem exhibiting thorns;

6. Leaves.

DETAILED DESCRIPTION OF THE VARIETY

The following is a description of 'POULac004', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULjoey', a rose variety from the same inventors described and illustrated in U.S. Plant Pat. No. 11,598 and issued on Oct. 24, 2000 are compared to 'POULac004' in Chart 1.

CHART 1

| | 'POULac004' | 'POULjoey' |
|---|---|---|
| General tonality. | Red Group 43B. | Blend of Orange-Red Group 31B and Red Group 39B. |

CHART 1-continued

| | 'POULac004' | 'POULjoey' |
|---|---|---|
| Petal count. | 25. | 55 to 65. |
| Bloom diameter. | 70 to 90 mm. | 50 to 60 mm. |

Parents: Unnamed seedling×unnamed seedling.

FLOWER AND FLOWER BUD

Blooming habit: Continuous.

Flower bud:

*Size.*—Upon opening, 30 mm in length from base of receptacle to end of bud. Bud diameter is 13 mm.

*Bud form.*—Pointed ovoid.

*Bud color.*—As sepals unfold, Red Group 46C. At ¼ opening, Red Group 46C.

*Sepals.*—Green Group 143A. Weak foliaceous appendages on three of the five sepals. Surfaces of sepals slightly pubescent. Stipitate glands are occasionally present on sepal undersides. Shape: Overall sepal shape is elliptical and slightly broad based. Sepal apex is aristate. Base is flat at union with peduncle. Margin: Sepal margin is entire. Size: 32 mm long×8 mm wide.

*Receptacle.*—Surface: Scantily pubescent. Shape: Urn-shaped. Size: 6 mm (h)×6 mm (w). Color: Yellow-Green Group 144A.

*Peduncle.*—Surface: With scant stipitate glands. Length: 40 to 50 mm average length. Diameter: Peduncle diameter is 2 mm. Color: Yellow-Green Group 144A. On plants grown under high light conditions, peduncle may exhibit intonations of Greyed-Red Group 178A. Strength: Somewhat strong. Texture: Peduncle surface is rough with stipitate glands.

*Borne.*—Typically 3 buds per stem.

*Anthocyanin.*—Greyed-Red Group 178A.

Flower bloom:

*Fragrance.*—None.

*Duration.*—As a pot plant, flowers last from 7 to 10 days.

*Size.*—Average flower diameter is 70 to 90 mm when open. Average flower depth is 24 mm.

*Form.*—Shape of flower when viewed from the side: Upon opening, upper part: Flattened convex. Upon opening, lower part: Convex. Open flower, upper part: Flattened convex. Open flower, lower part: Convex.

*Petalage.*—Average range: 25 to 28 petals under normal conditions with 14 petaloids.

Color:

*Upon opening, petals.*—Outermost petals: Outer Side: Red Group 46C. Inner Side: Red Group 43B. Innermost petals: Outer Side: Red Group 46C. Inner Side: Red Group 43B.

*Upon opening, basal petal spots.*—Outermost petals: Outer Side: White Group 155A. Inner Side: White Group 155A. Innermost petals: Outer Side: White Group 155A. Inner Side: White Group 155A.

*After opening, petals.*—Outermost petals: Outer Side: Red Group 46C. Inner Side: Red Group 43B. Innermost petals: Outer Side: Red Group 46C. Inner Side: Red Group 43B.

*After opening, basal petal spots.*—Outermost petals: Outer Side: White Group 155A. Inner Side: White Group 155A. Innermost petals: Outer Side: White Group 155A. Inner Side: White Group 155A.

General tonality: On open flower Red Group 43B. No change in the general tonality at the end of the $10^{th}$ day. Afterwards, general tonality is Red Group 43B.

Petals:

*Petal reflex.*—Medium.

*Petal edge.*—Entire.

*Shape.*—Apex is round; base is pointed. Overall petal shape is deltoid.

*Size.*—Petals are 32 mm in length by 30 mm wide.

*Petaloids.*—Quantity: 14. Size: 20 mm long; 10 mm wide. Color: Red Group 45A. Shape: Petaloids are falcate with obtuse petaloid apex.

*Thickness.*—Moderately thick.

*Arrangement.*—Formal.

Reproductive organs:

*Pistils.*—Length: 6 mm long. Quantity: 50. Color: Greyed-Yellow Group 160B.

*Pollen.*—Color: Yellow-Orange Group 15A. Quantity: Scant.

*Anthers.*—Size: 7 mm long. Color: Red Group 54A. Quantity: 114.

*Filaments.*—Color: Greyed-Yellow Group 162A. Length: 2 mm.

*Stigmas.*—Level in position with anthers. Color: Greyed-Yellow Group 162C.

*Styles.*—Color: Greyed-Yellow Group 160A.

*Seed formation.*—None observed.

PLANT

Plant growth: Moderate. The average plant height is 50 cm and the average plant width is 50 cm.

Stems:

*Color.*—Young wood: Yellow-Green Group 146C. Older wood: Yellow-Green Group 146C.

*Prickles.*—Incidence: 10 mm per 10 cm of stem. Size: Average length: 6 mm. Color: Greyed-Yellow Group 161A. Shape: Concave.

*Surface.*—Young wood: Smooth. Older wood: Smooth.

*Length.*—25 to 30 cm.

*Diameter.*—7 mm.

*Internodes.*—60 to 70 mm.

Plant foliage: Normal number of leaflets on normal leaves in middle of the stem: 5 leaflets.

*Leaf size.*—55 mm (l)×35 mm (w).

*Quantity.*—1 to 2 leaves per 10 cm of stem.

*Color.*—Upper Leaf Surface: Green Group 139A. Lower Leaf Surface: Yellow-Green Group 146B. Juvenile foliage: Upper Leaf Surface: Green Group 139A. Lower Leaf Surface: Yellow-Green Group 146B.

Plant leaves and leaflets:

*Stipules.*—Size: 30 mm long. Color: Yellow-Green Group 146B. Presence of stipitate glands: Scant. Shape: Linear. Margins: Entire.

*Petiole.*—Length: 30 mm. Diameter: 2 mm. Color: Yellow-Green Group 146B.

*Rachis.*—Color: Yellow-Green Group 146B. Margins: With stipitate glands.

*Leaflet.*—Edge: Serrated. Size: 45 mm in length by 40 mm in width. Shape: Broadly ovate. Apex shape is round to cuspidate. Base shape is round. Vein color: Yellow-Green Group 151A. Glossiness: Moderately glossy. Arrangement: Odd pinnate. Thickness: Somewhat thick. Venation: Reticulate.

Disease resistance: Average resistance to mildew, black spot, and Botrytis under normal growing conditions in Jackson County, Oreg.

Cold hardiness: 'POULac004' has been found to be resistant to damage from cold, heat and drought in USDA Zone 7.

It is claimed:

1. A new and distinct variety of rose plant of the Compact *Floribunda* class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

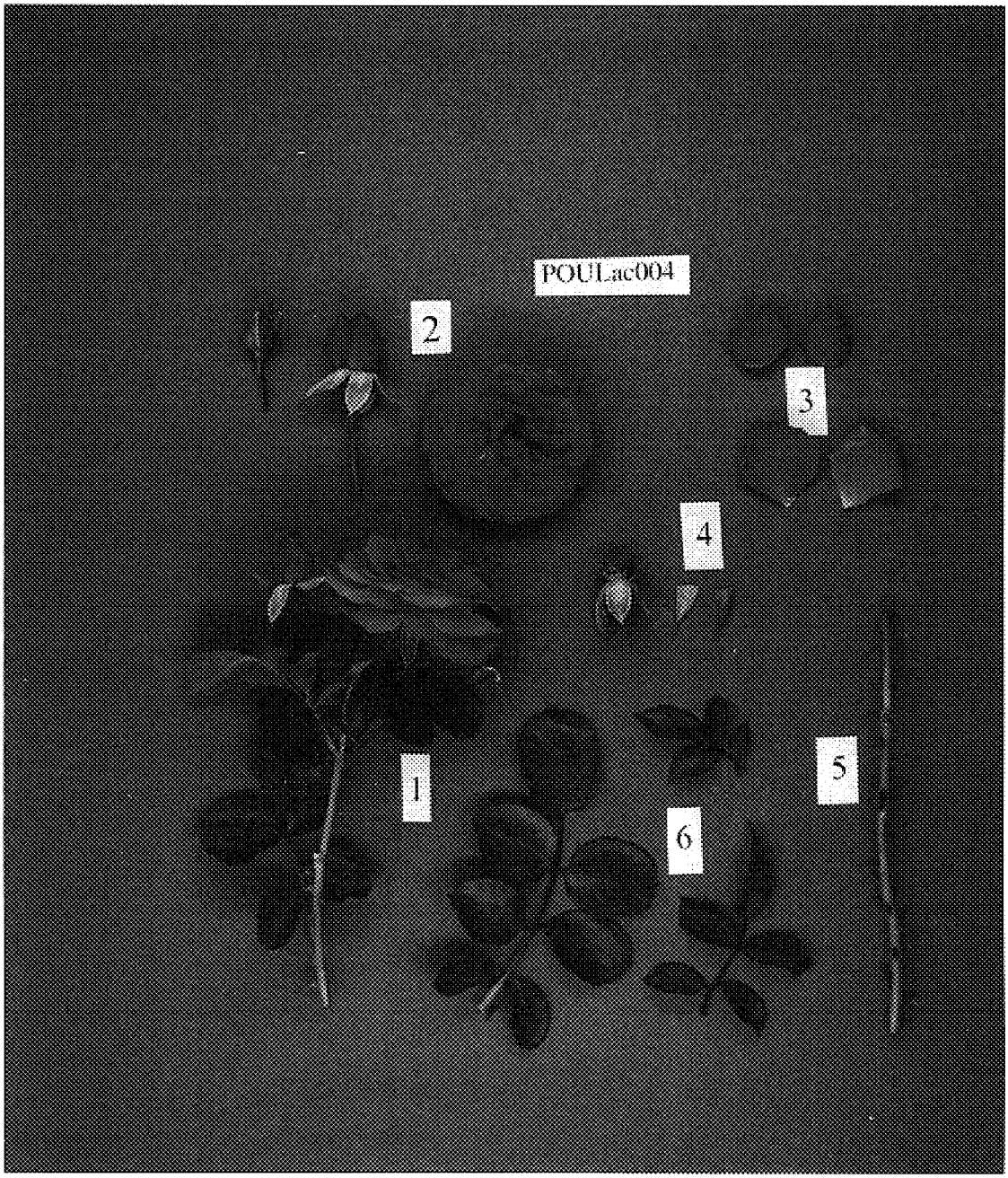
POULac004
2
3
4
1
5
6